United States Patent
Gibson et al.

(10) Patent No.: US 7,063,708 B2
(45) Date of Patent: Jun. 20, 2006

(54) INSERTION TOOL SYSTEM FOR AN ELECTRODE ARRAY

(75) Inventors: Peter Gibson, Lane Cove (AU); John Parker, Lane Cove (AU); Claudiu Treaba, Lane Cove (AU)

(73) Assignee: Cochlear Limited, Lane Cove (AU)

( * ) Notice: Subject to any disclaimer, the term of this patent is extended or adjusted under 35 U.S.C. 154(b) by 726 days.

(21) Appl. No.: 10/344,400

(22) PCT Filed: Mar. 19, 2002

(86) PCT No.: PCT/AU02/00333

§ 371 (c)(1),
(2), (4) Date: Feb. 11, 2003

(87) PCT Pub. No.: WO02/074211

PCT Pub. Date: Sep. 26, 2002

(65) Prior Publication Data

US 2003/0171758 A1 Sep. 11, 2003

(30) Foreign Application Priority Data

Mar. 19, 2001 (AU) .................................... PR3800
Jul. 30, 2001 (AU) .................................... PR6688

(51) Int. Cl.
*A61B 19/00* (2006.01)

(52) U.S. Cl. .................... 606/129; 606/108; 607/137

(58) Field of Classification Search ................ 606/108, 606/109, 129; 607/137
See application file for complete search history.

(56) References Cited

U.S. PATENT DOCUMENTS

| 4,532,930 | A | 8/1985 | Crosby et al. |
| 4,898,183 | A * | 2/1990 | Kuzma ........................ 607/137 |
| 5,443,493 | A | 8/1995 | Byers et al. |
| 5,545,219 | A | 8/1996 | Kuzma |
| 5,810,852 | A | 9/1998 | Greenberg et al. |
| 6,119,044 | A | 9/2000 | Kuzma |
| 6,149,657 | A | 11/2000 | Kuzma |
| 6,208,882 | B1 | 3/2001 | Lenarz et al. |

FOREIGN PATENT DOCUMENTS

| WO | WO 89/00870 | 2/1989 |
| WO | WO 93/24058 | 12/1993 |

OTHER PUBLICATIONS

International Search Report of PCT/AU02/00333, dated May 13, 2002.
International Preliminary Examination Report of PCT/AU02/00333, dated Sep. 20, 2002.

* cited by examiner

*Primary Examiner*—Eduardo C. Robert
*Assistant Examiner*—John Kim
(74) *Attorney, Agent, or Firm*—Jagtiani & Guttag

(57) ABSTRACT

A device (10) used for inserting an electrode array (15) into a cochlea of a subject. Particularly, the device (10) is adapted for insertion of electrode arrays (15) having an elongate carrier member (21) and a removable stylet (22) extending through the carrier member (21). The device includes a handle (11), an elongate positioning member (12) mounted to the handle (11), an actuator member (17) movable relative to the elongate positioning member (12), and at least one anchor member (16) connected to the actuator member (17) and engageable with the removable stylet (22). On insertion of the electrode array (15) into a subject's cochlea, the actuator member (17) can be moved relative to the elongate positioning member (12) to withdraw the removable stylet (22) from the carrier member.

15 Claims, 3 Drawing Sheets

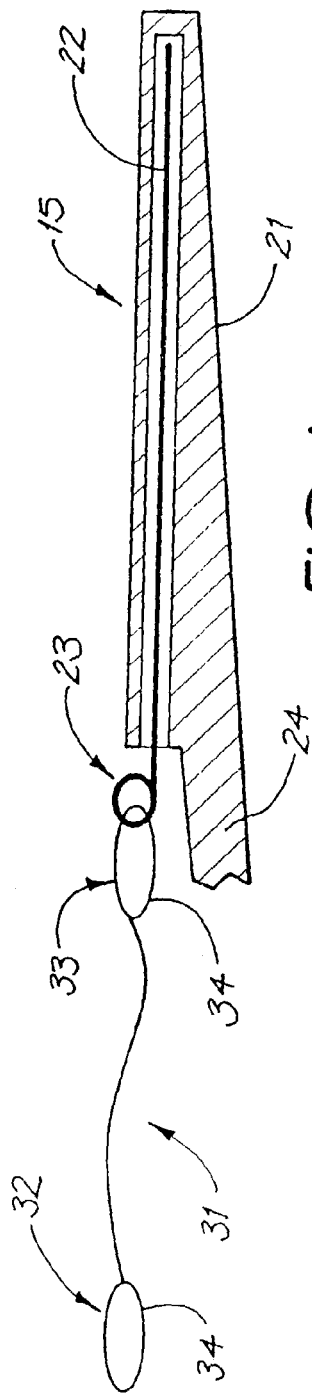
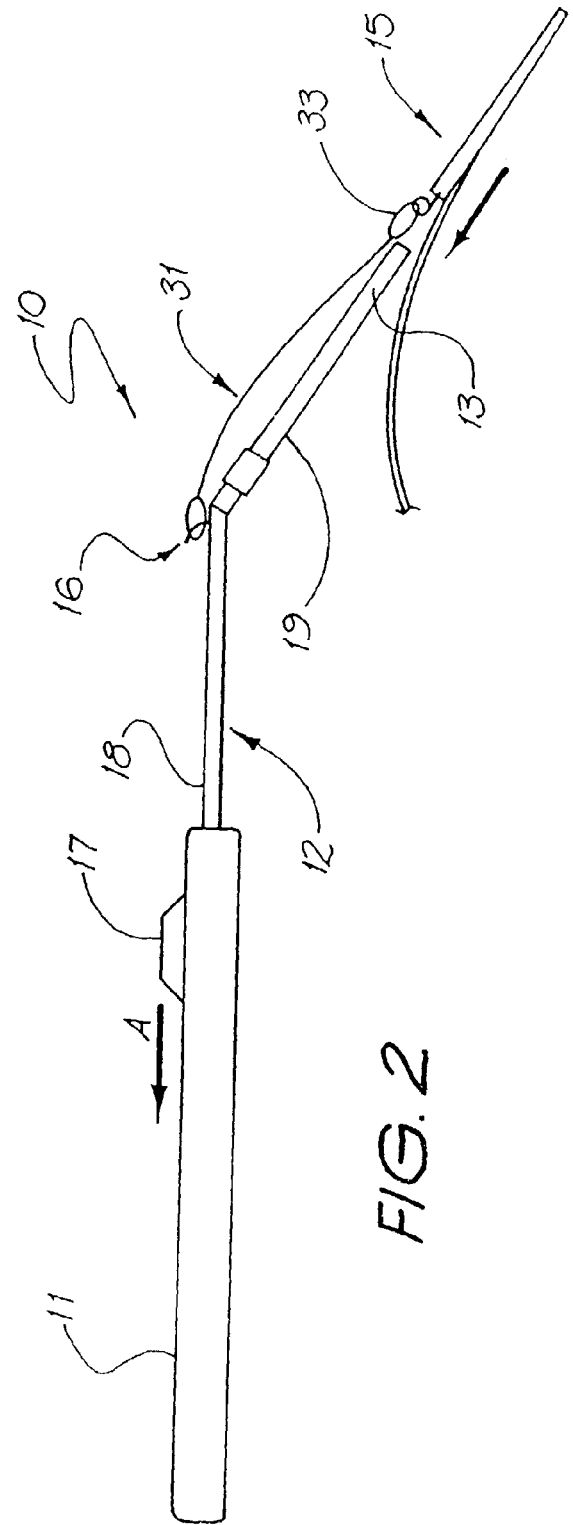

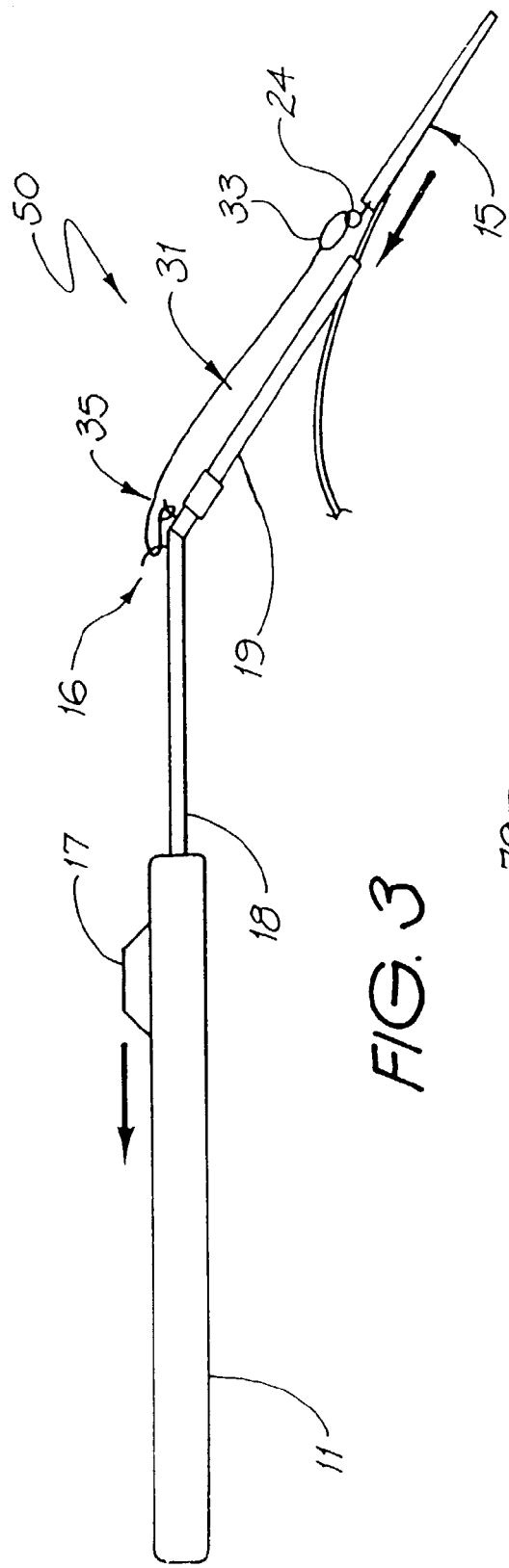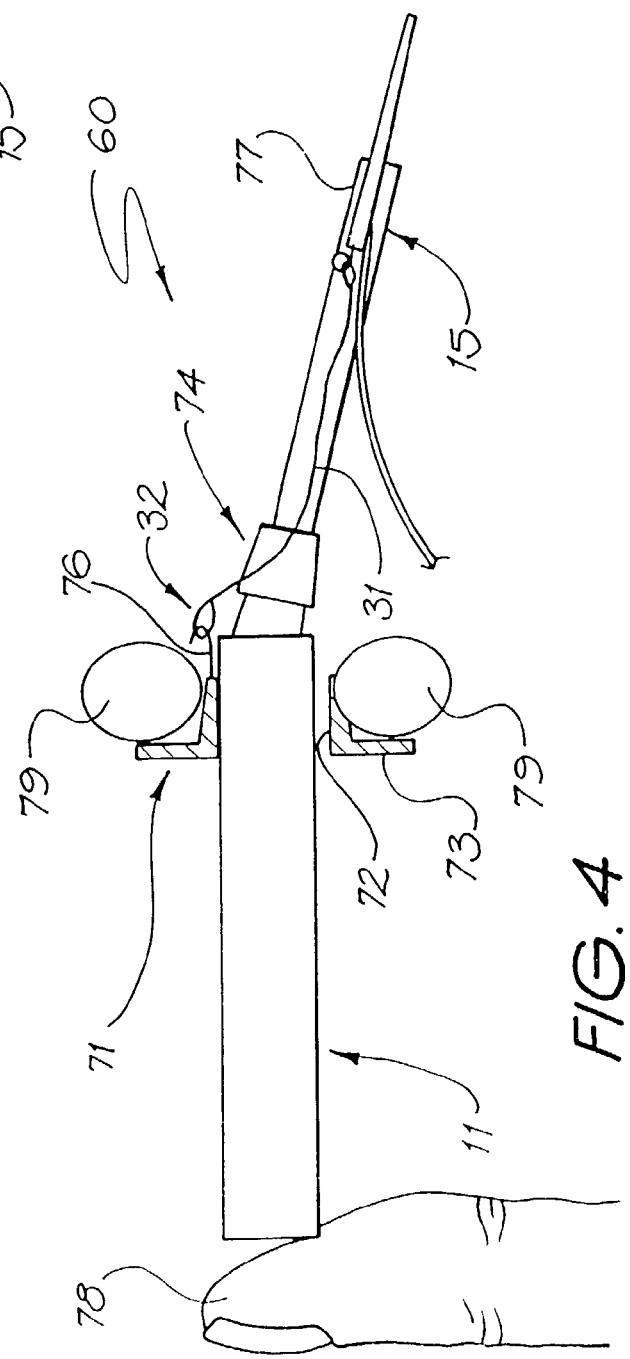

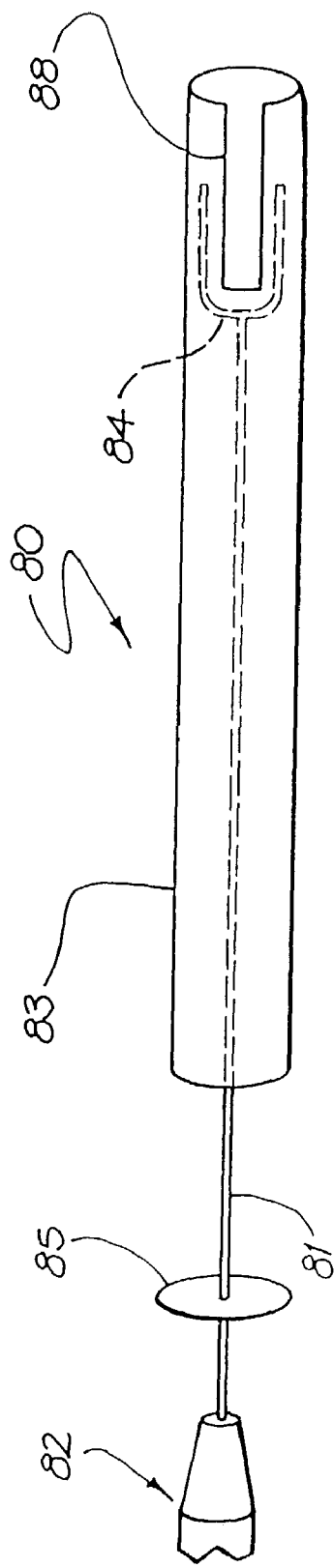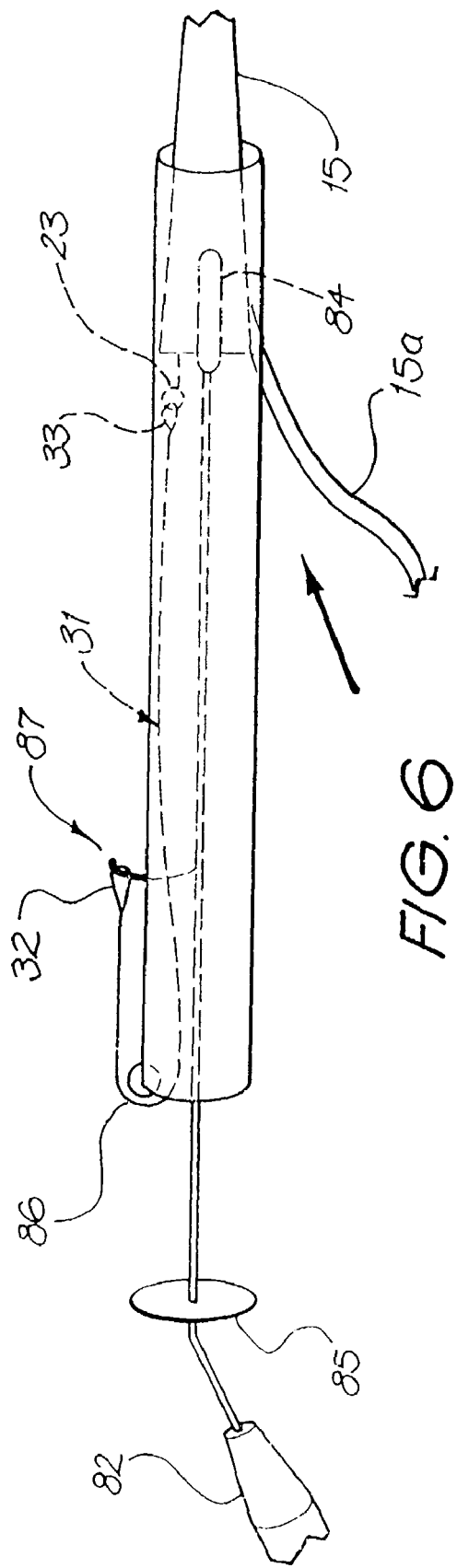

INSERTION TOOL SYSTEM FOR AN ELECTRODE ARRAY

CROSS-REFERENCE TO RELATED APPLICATION

This application is a National Phase Patent Application of International Application Number PCT/AU02/00333, filed on Mar. 19, 2002, which claims priority of Australian Patent Application Number PR 3800, filed on Mar. 19, 2001, and Australian Patent Application Number PR 6688, filed on Jul. 30, 2001

FIELD OF THE INVENTION

The present invention relates to a device and method for the insertion of an electrode array into a cochlea of a subject and, further, an electrode array adapted for insertion by said device.

BACKGROUND ART

In many people who are profoundly deaf, the reason for deafness is absence of, or destruction of, the hair cells in the cochlea which transduce acoustic signals into nerve impulses. These people are thus unable to derive suitable benefit from a conventional hearing aid systems, no matter how loud the acoustic stimulus is made, because there is damage to or absence of the mechanism for nerve impulses to be generated from sound in the normal manner.

It is for this purpose that cochlear implant systems have been developed. Such systems bypass the hair cells in the cochlea and directly deliver electrical stimulation to the auditory nerve fibres, thereby allowing the brain to perceive a hearing sensation resembling the natural hearing sensation normally delivered to the auditory nerve. U.S. Pat. No. 4532930, the contents of which are incorporated herein by reference, provides a description of one type of traditional cochlear implant system.

Typically, cochlear implant systems have consisted of essentially two components, an external component commonly referred to as a processor unit and an internal implanted component commonly referred to as a stimulator/receiver unit. Traditionally, both of these components have cooperated together to provide the sound sensation to a user.

The external component has traditionally consisted of a microphone for detecting sounds, such as speech and environmental sounds, a speech processor that converts the detected sounds, particularly speech, into a coded signal, a power source such as a battery, and an external transmitter coil.

The coded signal output by the speech processor is transmitted transcutaneously to the implanted stimulator/receiver unit situated within a recess of the temporal bone of the user. This transcutaneous transmission occurs via the external transmitter coil which is positioned to communicate with an implanted receiver coil provided with the stimulator/receiver unit.

This communication serves two essential purposes, firstly to transcutaneously transmit the coded sound signal and secondly to provide power to the implanted stimulator/receiver unit. Conventionally, this link has been in the form of an RF link, but other such links have been proposed and implemented with varying degrees of success.

The implanted stimulator/receiver unit traditionally includes a receiver coil that receives the coded signal and power from the external processor component, and a stimulator that processes the coded signal and outputs a stimulation signal to an intracochlear electrode assembly which applies the electrical stimulation directly to the auditory nerve producing a hearing sensation corresponding to the original detected sound.

Traditionally, the external componentry has been carried on the body of the user, such as in a pocket of the user's clothing, a belt pouch or in a harness, while the microphone has been mounted on a clip mounted behind the ear or on the lapel of the user.

More recently, due in the main to improvements in technology, the physical dimensions of the speech processor have been able to be reduced allowing for the external componentry to be housed in a small unit capable of being worn behind the ear of the user. This unit allows the microphone, power unit and the speech processor to be housed in a single unit capable of being discretely worn behind the ear, with the external transmitter coil still positioned on the side of the user's head to allow for the transmission of the coded sound signal from the speech processor and power to the implanted stimulator unit.

Together with improvements in available technology, much research has been undertaken in the area of understanding the way sound is naturally processed by the human auditory system. With such an increased understanding of how the cochlea naturally processes sounds of varying frequency and magnitude, there is a need to provide an improved cochlear implant system that delivers electrical stimulation to the auditory nerve in a way that takes into account the natural characteristics of the cochlea.

It is known in the art that the cochlea is tonotopically mapped. In other words, the cochlea can be partitioned into regions, with each region being responsive to signals in a particular frequency range, for example, the basal end of the cochlea is best responsive to high frequencies, and the apical end is best responsive to low frequency sounds. This property of the cochlea is exploited by providing the electrode assembly with an array of electrodes, each electrode being arranged and constructed to deliver a cochlea stimulating signal within a preselected frequency range to the appropriate cochlea region. The electrical currents and electric fields from each electrode stimulate the nerves disposed on the modiola of the cochlea.

It has been found that in order for these electrodes to be effective, the magnitude of the currents flowing from these electrodes and the intensity of the corresponding electric fields, are a function of the distance between the electrodes and the modiola. If this distance is relatively great, the threshold current magnitude must be larger than if the distance is relatively small. Moreover, the current from each electrode may flow in all directions, and the electrical fields corresponding to adjacent electrodes may overlap, thereby causing cross-electrode interference. In order to reduce the threshold stimulation amplitude and to eliminate cross-electrode interference, it is advisable to keep the distance between the electrode array and the modiola as small as possible. This is best accomplished by providing the electrode array in the shape which generally follows the shape of the modiola. Also, this way the delivery of the electrical stimulation to the auditory nerve is most effective as the electrode contacts are as close to the auditory nerves that are particularly responsive to selected pitches of sound waves.

In order to achieve this electrode array position close to the inside wall of the cochlea, the electrode needs to be designed in such a way that it assumes this position upon or immediately following insertion into the cochlea. This is a challenge as the array needs to be shaped such that it assumes a curved shape to conform with the shape of the modiola and must also be shaped such that the insertion process causes minimal trauma to the sensitive structures of the cochlea. In this sense, it is desirable that the electrode array is in a generally straight configuration during the insertion procedure.

Several procedures have been adopted to provide an electrode assembly that is relatively straightforward to insert while adopting a curved configuration following insertion in the cochlea: In this regard, it is known to make an electrode array that includes a spiral-shaped carrier which has a natural spiral shape generally conforming to the configuration of a cochlea. Such an array may also include a straightening element or stylet. This enables the carrier to be inserted into the cochlea in a straight configuration. The stylet is then removed as the carrier is moved into the cochlea such that it begins to take on its natural spiral-shape.

Typically the stylet is removed following the insertion of the electrode array into the cochlea by clamping an exposed end of the stylet with tweezers and gradually removing the stylet. It may also be possible for the stylet to be removed while simultaneously introducing the electrode array into the cochlea. In either case, however, the technique is difficult to coordinate and requires both hands of a surgeon to perform.

A number of tools have been developed to assist in the insertion of the electrode array and/or subsequent removal of the straightening element. Typically, such devices have been difficult to use and have required complex mechanisms to achieve the desired result. This has resulted in tools that are difficult to manufacture, difficult to clean for re-use as well as having an increased probability of failure due to their complexity.

The present invention is directed to an insertion tool for an electrode assembly which is constructed to overcome the abovementioned problems of prior devices.

In providing the above description of the prior art, the present applicant is not conceding that any or all of the above description is part of the present common general knowledge of a person skilled in the art of the present invention in Australia.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY OF THE INVENTION

According to a first aspect, the present invention is a device for inserting an electrode array into a cochlea of a subject, the electrode array having an elongate carrier member and a removable means extending through the carrier member for at least a portion thereof, the device including a handle, an elongate positioning member mounted to the handle, an actuator member movable relative to the elongate positioning member, and at least one anchor member connected to the actuator member and engageable with the removable means, wherein on insertion of the electrode array into a subject's cochlea, the actuator member can be moved relative to the elongate positioning member to withdraw the removable means from the carrier member.

In this aspect, the device can be adapted to insert an electrode array having a removable means positioned therein, wherein the removable means has a capture member located at or adjacent a proximal end of the removable means.

According to a second aspect, the present invention is an electrode array for insertion into a cochlea of a subject, the electrode array including an elongate carrier member having a plurality of electrodes mounted thereon and a removable means extending through the carrier member for at least a portion thereof, the removable means further having a capture member positioned at or adjacent a proximal end of the removable means.

In a third aspect, the present invention is a method of inserting an electrode array into a cochlea of a subject and, further, removing a removable means of the electrode array following insertion using a device of the first aspect, the method including the steps of:

(a) loading an electrode array having a removable means onto the positioning member;

(b) connecting one end of a tie member, to the anchor member and another end of the tie member to the removable means of the electrode array;

(c) gradually introducing the electrode array into the cochlea; and (d) causing or allowing the removable means to be relatively withdrawn from the electrode array.

Typically, the positioning member comprises a proximal portion located adjacent the handle and a distal portion extending from said proximal portion to a distal end. The distal portion may be angled relative to the proximal portion and the handle such that when the device is in use, the distal portion does not obstruct a surgeon's view of the cochlea.

In a preferred embodiment, at least the distal portion of the positioning member is rotatably movable relative to the handle and the proximal portion of the positioning member. This embodiment has the advantage that when an electrode array is loaded onto the positioning member, rotation of the positioning member will change the orientation of the electrode array to a particular orientation suitable for an individual surgery. Alternatively, the entire positioning member may be rotatably movable relative to the handle.

In a further embodiment, the positioning member may be removable from the handle.

The elongate positioning member may have a lumen extending therethrough. In one embodiment, the elongate positioning member can be adapted to at least partially enter a cochleostomy prepared by a surgeon. In another embodiment, at least the distal end of the elongate positioning member be shaped such that it abuts with the bone around the cochleostomy.

Preferably, the anchor member is positioned in the proximal portion of the positioning means. In another embodiment, the anchor member can be positioned in the proximal portion adjacent its connection with the distal portion of said member. In another embodiment, the anchor member may be positioned in the distal portion of the elongate member.

The anchor member may comprise a hook or a loop-like structure which is adapted to engage with a tie member extending from the removable means of the electrode array. The anchor member may be made of any suitable material such as a plastics material or a metal or metal alloy. Alternatively, the anchor member may comprise a pulley member which receives and engages the tie member.

The tie member is preferably a flexible member and may be made from any suitable material which includes, but is not limited to, a suture-type material. Such material has the advantage that it is biocompatible.

The tie member preferably has one end which is engageable with the anchor member and then extends distally to a second end which is engageable with the capture member located at or adjacent the proximal end of the removable means of the electrode array.

In another embodiment, the tie member can extend proximally from the removable means, around the anchor member and then back distally to a secondary secured anchor mounted to the positioning member. In this embodiment, the tie member can move slidably around the anchor member upon movement of the actuator member relative to the handle.

In another embodiment, the anchor member can comprise a pulley member which receives the tie member in one embodiment, the secondary secured anchor can be engaged with the proximal end of the tie member. The secondary secured anchor can be mounted to the distal portion of the positioning member.

In another embodiment, the anchor member may be mounted on the actuator member. In this embodiment, the tie member preferably extends proximally from the removable means, around a pulley member or other tie member sliding member, and then back distally to the anchor member. The pulley member or other tie member sliding member can be mounted on the elongate positioning member. It will be appreciated that this member could also be mounted on the handle if the elongate positioning member is movable relative to the handle. In this embodiment, movement of the actuator member in the distal direction relative to the positioning member results in the tie member withdrawing the removable means from the array.

Preferably, the ends of the tie member form secure connections with the respective anchor member and capture members. Either or both connections may be made at any stage during the manufacture of the device of the present invention or alternatively could be made immediately prior to a surgical procedure by the surgeon.

The tie member may be connected in a number of ways. For example, in a preferred embodiment, the anchor member and the capture member comprise hooks and the ends of the tie member form loops which may extend over and engage with the anchor member and the capture member. Alternatively, the tie member may, in its entirety, form a single loop which at both ends extends over and engages with the anchor and capture members. Alternatively, the tie member may include a bead member at each end such that the bead members engage with complementary structures on the anchor member and the capture member.

In a further embodiment, the anchor member may also comprise a channel, said channel extending along at least a portion of the length of the positioning member. In this embodiment, the tie member is received within the channel and may be retained therein by friction fit.

In a preferred embodiment, the positioning member includes a slot at its distal end, said slot adapted to receive and engage a proximal end of the electrode array. In a further embodiment, the slot is positioned in the distal portion of the positioning member. This enables insertion of the electrode array into the cochlea. Once in position, the electrode array may be caused to slide from this slot and into position within the cochlea of a subject.

In another embodiment, the distal portion of the positioning member may be provided with an electrode array already mounted thereon. For insertion into the cochlea of a subject, a surgeon would assemble the distal portion of the positioning member, including the electrode array together with the handle. In this embodiment, the action of assembling the various components together results in the proximal end of the tie member engaging with the anchor means.

In another embodiment, the actuator member may have a distal end adapted to engage with the electrode array. For example, the distal end may be fork-shaped and adapted to grip the carrier member of the array. In this embodiment, the actuator member preferably has a stopper member at a position distal its distal end. The stopper is preferably adapted to prevent the actuator member from moving beyond a predetermined distance relative to the positioning member.

The actuator member of the present invention may comprise a slide member which is slidably movable along a length of the handle.

The slide member may be connected to the anchor member by a connector means which may comprise a number of structures including, but not limited to, a flexible cord, a solid rod or alternatively, a continuation of the tie member described above. The latter embodiment is envisaged particularly where the anchor member acts as a pulley. The tie member would engage with and extend over the pulley to a connection point with the actuator member.

The actuator member may include at least one finger grip member to enable manipulation by a surgeon.

Typically, the actuator member may be moved from a first location on the handle adjacent the positioning member to a second location on the handle distal the positioning member by the surgeon. Movement in this manner will cause the connection means to draw the anchor member, or in certain embodiments, the tie member, towards the handle.

In a preferred embodiment, the tie member is connected to both the anchor member and the capture member of the removable means, such that drawing the anchor member towards tile handle causes the removable means to be withdrawn from the electrode array. Preferably, the actuator member moves relatively smoothly along a length of the handle and without the need for application of a great amount of pressure. In this way, a surgeon using the device of the invention may move the actuator member with the same hand as holds the device. It is envisaged that the actuator member may be moved by an index, or other, finger or thumb of a surgeon using the device.

The elongate carrier of the electrode array may be straight or curved. Further, the elongate carrier member may be adapted to adopt a spiral configuration.

Preferably, the elongate carrier member has a first configuration selected to allow the electrode array to be inserted into the cochlea of a subject and at least a second configuration wherein said electrode array applies the preselected tissue stimulation. As is desirable to insert an electrode array into a cochlea in an initially straight configuration, it is preferred that the first configuration of the electrode array is substantially straight. Moreover, it is preferred that the elongate carrier member adopts a spiral configuration when in the second configuration.

The removable means of the electrode array may be a stiffening means. In this embodiment, the elongate carrier member of the electrode array has a lumen which receives the removable stiffening means, the stiffening means having a configuration selected for biasing the elongate carrier member into the first configuration The elongate carrier member may be formed from a resiliently flexible and biocompatible material. Furthermore, it is preferred that the elongate carrier member is preformed from a plastics material with memory and, moreover, is preformed to the second configuration. Alternatively, the material may be a biocompatible silicone or suitable elastomeric material, such as a polyurethane.

In one embodiment, the stiffening means may comprise a stiffening element formed from a non-bioresorbable material. In this embodiment, the stiffening element may comprise a metallic stylet extending through the receiving portion of the body of the elongate carrier member. Preferably, the stylet is formed from a biocompatible metal or metallic alloy. An example of a suitable metal is platinum.

The stiffening element may be formed from a shape memory or heat sensitive material such as a bimetallic element or shape memory alloy (such as nickel/titanium) and shaped to take a straight or substantially straight configuration at room temperature but which bends into another shape upon exposure to body temperature.

The lumen of the elongate carrier member may extend at least into, and more preferably through, the body of the elongate carrier member.

The assembly or device according to the respective aspects of the invention can further include a stiffening sheath that envelops the elongate carrier member of the electrode array. The sheet may be made of a material that is relatively stiffer than the material of the body of the elongate carrier member. Where used, the stiffening sheath can, in combination with the stiffening element, act to bias the elongate carrier member into the first configuration. Removal of either the stiffening element or stiffening sheath, in this embodiment, preferably results in the elongate carrier member adopting the fully curved second configuration desired of an implant for insertion into the cochlea.

BRIEF DESCRIPTION OF THE DRAWINGS

FIG. 1 is a side elevation view of a device according to the present invention;

FIG. 2 is a side elevational and partly cut-away view of the device according to the present invention;

FIG. 3 is a side elevational view of another embodiment of a device according to the present invention;

FIG. 4 is a side elevational view of still further embodiment of a device according to the present invention;

FIG. 5 is a bottom view of yet another embodiment of the device of the present invention; and FIG. 6 is a side view of the device of FIG. 5 in use.

PREFERRED MODE OF CARRYING OUT THE INVENTION

One embodiment of an insertion device according to the present invention is depicted generally as 10 in FIG. 2.

The device 10 comprises a handle 11 and an elongate positioning member 12. The positioning member 12 has a proximal portion 18 and a distal portion 19 that extends to a distal end 13. The distal portion 19 receives and supports an electrode array 15 to allow positioning of the array 15 within a cochlea of a subject.

The device 10 further includes an anchor 16 which is positioned at a location alone the length of the positioning member 12 and extends through a slot (not visible in FIG. 2) in that member. The anchor 16 is connected to a finger actuable control 17 that extends outwardly through a slot in the handle 11 from a slide member (not visible) that extends through the handle 11 and the proximal portion 18 of the positioning member 12 to the anchor 16.

Electrode array 15 includes an elongate carrier 21 with a plurality of electrodes (not shown for reasons of clarity) mounted thereon. The electrode array 15 also includes a stylet 22 which, in the present embodiment, is designed to keep the electrode array 15 in a straight configuration while it is being inserted into a cochlea of a subject. The stylet 22 has a capture member 23 positioned at its proximal end.

The device of the present invention includes a tie member 31 which has a first end 32 and a second end 33. As depicted in FIG. 2, the first end 32 is engageable with anchor 16 and the second end 33 is engageable with capture member 23 of the stylet 22. Tie member 31 is preferably a flexible cord made from a suture-type material. Use of other wire materials, such as platinum wire can also be envisaged.

The tie member 31 may be connected in a number of ways. For example, as depicted, the ends of the tie member 31 form loops 34 which may extend over and engage respectively with anchor 16 and capture member 23.

In use, the finger actuable control 17 is moved from a first location on handle 11 adjacent positioning member 12 to a second location on the handle 11 distal the positioning member 12. Movement in this manner will cause the rod member to draw the anchor 16 relatively towards the handle 11.

As depicted in FIG. 2, the positioning member 12 comprises a proximal portion 18 located adjacent handle 11 and a distal portion 19 extending from said proximal portion 18. The distal portion 19 is angled relative the proximal portion 18 and the handle 11 such that when the device 10 is used to insert an electrode array 15, the distal portion 19 does not obstruct the surgeon's view of the cochlea. The distal portion 19 is further rotatably movable relative to the handle 11 and the proximal portion 18 such that when an electrode array 15 is loaded onto the distal end 13 of positioning member 12, rotation of the distal portion 19 will change the orientation of the electrode array 15 to a particular orientation suitable for an individual surgery.

As further shown in FIG. 2, the anchor 16 is positioned in the region of the proximal portion 18 of the positioning member 12.

While, for clarity, FIG. 2 depicts the tie member 31 as free from the distal portion 19 of the positioning member 12 it is to be understood that the tie member 31 may be received by a channel (not shown) in the distal portion 19. The tie member 31 can be retained within the channel by friction fit or alternatively may be loosely contained within the confines of the channel.

The distal portion 19 further includes a slot (not shown) that is adapted to receive and engage a proximal end 24 of the electrode array 15. This provides a means to introduce the electrode array 15 into the cochlea of a subject.

In use, it is preferred that the electrode array 15 is inserted into the cochlea in a straight configuration and when within the cochlea, caused to take on a spiral configuration. This is often achieved by providing the electrode array with a straightening stylet 22. As the electrode array 15 is advanced into the cochlea, a surgeon will typically simultaneously withdraw the stylet 22 such that the array 15 is free to take on its spiral configuration, the preferred configuration of an electrode array when in position within a cochlea.

The stylet is removed by the surgeon using the finger actuable control 17 to move the slide relative to the handle in a direction depicted by A, which in turn draws anchor 16 toward handle 11. As the tie member 31 is connected to both the anchor 16 and the stylet 22, the stylet 22 is gradually pulled free from the electrode array 15. The entire device is then withdrawn slowly from the surgical site. The electrode array 15 is retained within the cochlea due to the slight spring force of its pre-curved shape which is greater than the slight friction fit of the electrode array 15 in the slot of the distal portion 19. The electrode array 15 therefore slides out of the distal portion 19 as the device 10 is withdrawn.

In an alternative arrangement depicted in FIG. 3, the device 50 is essentially identical to device 10 except that the tie member 31 extends proximally from its connection with the stylet 22, around the anchor member 16 and then extends distally before being secured to a secondary secured anchor 35. On using the device 50, retraction of the actuable control 17 results in the tie member 31 sliding around the anchor 16. In essence, the anchor 16 acts as a pulley member. Because of the advantage provided by the anchor 16, a movement of X mm of the control 17 results in a movement of 2X mm of the stylet 22. This is advantageous as it decreases the necessary finger movement by the surgeon during use of the device. For example, the control 17 need only be moved relative to the handle 11 by a distance of 16 mm to cause the stylet to move a distance of 32 mm.

FIG. 4 depicts a further embodiment of the device designated as 60. In the case of device 60, the actuable control member 71 comprises a cylindrical member 72 positioned outside and relatively movable to the handle 11. The cylindrical member 72 has an annular finger abutment member 73 that, in use, can be pulled back relative to the handle by the index and middle fingers of the surgeon. In this regard, the device 60 can be gripped in a manner similar to that used to grip and control a syringe, with the thumb 78 used to stabilise the end of the handle 11. As depicted, the tie member 31 extends proximally from its connection with the stylet 22 through the inside of the positioning member 74 to an anchor member 76 connected to the cylindrical member 72. In the depicted embodiment, the positioning member 74 is mounted to the handle 11 but is relatively rotatable thereto.

In use, the tie member 31 would be firstly fed through the hollow positioning member 74 to load the electrode array 15 into a slot formed adjacent its distal end 77. The positioning member 74 would then be mounted on the handle 11 and rotated relative thereto so as to be at the orientation desired for the surgery. The control 71 would then be slid forward to an end stop such that the anchor member 76 is relatively close to the distal end of the handle 11. The loop 32 at the proximal end of the tie member 31 can then be engaged with the anchor member 76. The device 60 can then be held in a syringe-style manner with the thumb 78 on the proximal end of the handle 11 and the index and middle fingers 79 on the control 71. The device can then be moved relatively forward to commence insertion of the array 15 through the cochleostomy. The control 71 can then be moved relatively proximally to the handle 11 using the index and middle fingers 79 to withdraw the stylet 22 from its lumen within the array 15. Once insertion is complete, the device 60 can be withdrawn, leaving the array 15 in place within the cochlea.

Two insertion techniques are available through use of the device 60. In the standard insertion technique, the electrode array 15 is inserted fully and then the stylet 22 is withdrawn. In another technique, the array 15 can be inserted until the distal tip of the array 15 is near the back of the basal turn of the cochlea. Once there, the stylet 22 can begin to be withdrawn by moving the control 71 relatively proximally while still continuing to advance the array into the cochlea using the device 50. Using this technique, the electrode array 15 preferably follows a trajectory which is along or near the middle of the lumen or the scala tympani of the cochlea. This avoids or lessens pressure on the outside (lateral) wall of the cochlea.

Another device arrangement is depicted generally as 80 in FIGS. 5 and 6. In this arrangement, the actuator member comprises a push rod 81 extending distally from a distal end of a handle 82. The push rod 81 extends through a positioning member in the form of guide tube 83 and ends in a fork 84. As depicted in FIG. 6, the fork 84 can grip the proximal end of the electrode array 15. The electrode leads 15a of the array 15 extend out of the guide tube through a slot 88 formed adjacent the distal end of the tube 83.

The device 80 includes a stopper 85 on the push rod 81 that comes into abutment with the proximal end of the guide tube 83 if the push rod 81 is moved in a proximal direction relative to the guide tube 83.

On mounting of the array 15 within the guide tube 83 and into the tines of the fork 84, the tie member 31 is connected to the device 80 as depicted in FIG. 6. The tie member 31 extends proximally from its second end 33 connected to the capture member 23 of the stylet. The tie member extends around a pulley member 86 mounted on the guide tube 83 and back distally to an anchor 87 on the push rod 81. The anchor 87 extends outwardly through a slot formed in the guide tube 83.

During use, the device 80 is used to advance the array into the cochleostomy. Once the distal end of the guide tube 83 stops on the bone around the cochleostomy, the push rod 81 can be advanced further to push the array 15 out of the guide tube 81. This results in the anchor 87 moving forwardly relatively to the pulley 86 so causing the stylet to be withdrawn from the array 15. Each 1 mm movement forward of the push rod 81 results in a 2 mm withdrawal of the stylet from the array 15.

An advantage of device 80 is that the stylet is automatically withdrawn on advancement of the array 15 in to the cochlea.

One of the further advantages of the present invention is that the electrode array 15 is readily removable from the insertion device prior to use. This is advantageous as it is envisaged that some surgeons may choose not to use the device or find it unsuitable for use in certain circumstances. To remove the electrode array, the surgeon needs simply to cut the tie member 31 and carefully remove the array 15 from the positioning member 12. Once removed, the array can be inserted by hand, using standard devices such as jewellery forceps.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A device for inserting an electrode array into a cochlea of a subject, the electrode array having an elongate carrier member and a removable means extending through the carrier member for at least a portion thereof, the device including a handle, an elongate positioning member mounted to the handle, an actuator member movable relative to the elongate positioning member, and at least one anchor member connected to the actuator member and engageable with the removable means, wherein on insertion of the electrode array into a subject's cochlea, the actuator member can be moved relative to the elongate positioning member to withdraw the removable means from the carrier member.

2. The device of claim 1 adapted to insert an electrode array having a removable means positioned therein, wherein the removable means has a capture member located at or adjacent a proximal end of the removable means.

3. The device of claim 1 or claim 2 wherein the positioning member comprises a proximal portion located adjacent the handle and a distal portion extending from said proximal portion to a distal end.

4. The device of claim 1 wherein the anchor member is positioned in the proximal portion or the distal portion of the positioning member.

5. The device of claim 1 wherein the anchor member is positioned on the actuator member.

6. The device of claim 1 wherein the anchor member is adapted to engage with a tie member extending from the removable means of the electrode array.

7. The device of claim 6 wherein the tie member is a flexible member made from a biocompatible material.

8. The device of claim 6 or claim 7 wherein the tie member has one end which is engageable with the anchor member and then extends distally to a second end which is engageable with the capture member located at or adjacent the proximal end of the removable means of the electrode array.

9. The device of claim 6 wherein the tie member extends proximally from the removable means, around the anchor member and then back distally to a secondary secured anchor mounted to the positioning member.

10. The device of claim 1 wherein the actuator member has a distal end adapted to engage with the electrode array.

11. The device of claim 10 wherein the actuator member has a stopper member at a position distal its distal end said stopper member adapted to prevent the actuator member from moving beyond a predetermined distance relative to the positioning member.

12. The device of claim 1 wherein the actuator member comprises a slide member which is slidably movable along a length of the handle.

13. The device of claim 1 wherein the slide member is connected to the anchor member by a connector means.

14. The device of claim 13 wherein the connector means is selected from a flexible cord, a solid rod or a continuation of the tie member.

15. A method of inserting an electrode array into a cochlea of a subject and, further, removing a removable means of the electrode array following insertion using a device of claim 1, the method including the steps of:

(a) loading an electrode array having a removable means onto the positioning member;

(b) connecting one end of a tie member to the anchor member and another end of the tie member to the removable means of the electrode array;

(c) gradually introducing the electrode array into the cochlea; and (d) causing or allowing the removable means to be relatively withdrawn from the electrode array.

* * * * *